US006297235B1

(12) United States Patent
Ladduwahetty et al.

(10) Patent No.: US 6,297,235 B1
(45) Date of Patent: *Oct. 2, 2001

(54) TRIAZOLOPYRIDAZINE DERIVATIVES FOR TREATING ANXIETY AND ENHANCING COGNITION

(75) Inventors: Tamara Ladduwahetty, London; Kevin John Merchant, Stevenage; Francine Sternfeld, London; Leslie Joseph Street, Harlow, all of (GB)

(73) Assignee: Merck Sharp & Dohme Ltd., Hoddeson (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/190,751

(22) Filed: Nov. 12, 1998

Related U.S. Application Data

(63) Continuation-in-part of application No. 09/140,948, filed on Aug. 27, 1998.

(30) Foreign Application Priority Data

Aug. 28, 1997 (GB) .................................... 9718254

(51) Int. Cl.[7] .................... A61K 31/5025; C07D 487/04
(52) U.S. Cl. .................................. 514/228.5; 514/233.2; 514/248; 544/61; 544/118; 544/236
(58) Field of Search ................ 544/236, 61, 118; 514/248, 228.5, 233.2

(56) References Cited

U.S. PATENT DOCUMENTS

| 4,260,756 | * | 4/1981 | Moran et al. | 544/236 |
| 4,654,343 | * | 3/1987 | Albright et al. | 514/248 |
| 5,905,079 | * | 5/1999 | Sargent et al. | 514/248 |

FOREIGN PATENT DOCUMENTS

| WO 98/04559 | 5/1998 | (WO) . |
| WO 98/04560 | 5/1998 | (WO) . |

OTHER PUBLICATIONS

Marczynski, *Medline Abstract* for *Brain Research Bulletin* 45(4) p. 341–379 (1998).*
McNamara et al, *Psychobiology*, 21, p. 101–108, 1993.*
Lindner, Abstract for *Neurobiol. Learn. Mem.* , 68, p203–220, 1997.*
Allain et al., *Fundam. Clin. Pharmacol.* 12, p13–29, 1998.*
Cain et al., *Behavioural Brain Research* 111, p. 125–137, 2000.*

* cited by examiner

*Primary Examiner*—Emily Bernhardt
(74) *Attorney, Agent, or Firm*—Shu Muk Lee; David L. Rose

(57) ABSTRACT

A compound of formula I, or a salt or prodrug thereof:

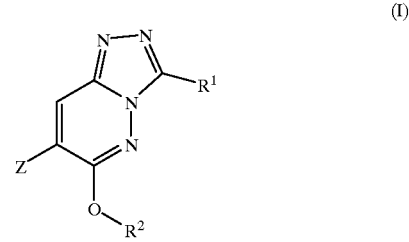

(I)

wherein:
Z represents $C_{1-6}$ alkyl, $C_{3-7}$ cycloalkyl, $C_{4-7}$ cycloalkenyl, aryl, $C_{3-7}$ heterocycloalkyl, heteroaryl or di($C_{1-6}$)alkylamino, any of which groups may be optionally substituted;

$R^1$ represents an optionally substituted five-membered heteroaromatic ring selected from oxazole, thiazole, isoxazole, isothiazole, imidazole, pyrazole, oxadiazole, thiadiazole, triazole and tetrazole; or $R^1$ represents an optionally substituted six-membered heteroaromatic ring selected from pyrazine, pyrimidine and pyridazine; and $R^2$ represents cyano($C_{1-6}$)alkyl, hydroxy($C_{1-6}$)alkyl, $C_{3-7}$ cycloalkyl($C_{1-6}$)alky, propargyl, $C_{3-7}$ heterocycloalkylcarbonyl($C_{1-6}$)alkyl, aryl($C_{1-6}$)alkyl or heteroaryl($C_{1-6}$)alkyl, any of which groups may be optionally substituted; its use in treating anxiety and pharmaceutical compositions comprising it; a subclass of compounds which are useful in enhancing cognition, such as Alzheimer's Disease, is also disclosed.

8 Claims, No Drawings

TRIAZOLOPYRIDAZINE DERIVATIVES FOR TREATING ANXIETY AND ENHANCING COGNITION

CROSS-REFERENCE TO RELATED APPLICATIONS

This is a continuation-in-part of application Ser. No. 09/140,948, filed Aug. 27, 1998, which claimed to priority under 35 U.S.C. §119 to Great Britain Application No. 97/18254.7, filed Aug. 27, 1997, the contents of both applications being hereby incorporated by reference.

The present invention relates to a class of substituted triazolo-pyridazine derivatives and to their use in therapy. More particularly, this invention is concerned with substituted 1,2,4-triazolo[4,3-b]pyridazine derivatives which are ligands for $GABA_A$ receptors and are therefore useful in the therapy of deleterious mental states.

Receptors for the major inhibitory neurotransmitter, gamma-aminobutyric acid (GABA), are divided into two main classes: (1) $GABA_A$ receptors, which are members of the ligand-gated ion channel superfamily; and (2) $GABA_B$ receptors, which may be members of the G-protein linked receptor superfamily. Since the first cDNAs encoding individual $GABA_A$ receptor subunits were cloned the number of known members of the mammalian family has grown to thirteen (six α subunits, three β subunits, three γ subunits and one δ subunit). It may be that further subunits remain to be discovered; however, none has been reported since 1993.

Although knowledge of the diversity of the $GABA_A$ receptor gene family represents a huge step forward in our understanding of this ligand-gated ion channel, insight into the extent of subtype diversity is still at an early stage. It has been indicated that an α subunit, a β subunit and a γ subunit constitute the minimum requirement for forming a fully functional $GABA_A$ receptor expressed by transiently transfecting cDNAs into cells. As indicated above, a δ subunit also exists, but is present only to a minor extent in $GABA_A$ receptor populations.

Studies of receptor size and visualisation by electron microscopy conclude that, like other members of the ligand-gated ion channel family, the native $GABA_A$ receptor exists in pentameric form. The selection of at least one α, one β and one γ subunit from a repertoire of thirteen allows for the possible existence of more than 10,000 pentameric subunit combinations. Moreover, this calculation overlooks the additional permutations that would be possible if the arrangement of subunits around the ion channel had no constraints (i.e. there could be 120 possible variants for a receptor composed of five different subunits).

Receptor subtype assemblies which do exist include, amongst many others, $α1β2γ2$, $α2β2/3γ2$, $α3βγ2/3$, $α2βγ1$, $α5β3$, $γ2/3$, $α6βγ2$, $α6βδ$ and $α4βδ$. Subtype assemblies containing an α1 subunit are present in most areas of the brain and are thought to account for over 40% of $GABA_A$ receptors in the rat. Subtype assemblies containing α2 and α3 subunits respectively are thought to account for about 25% and 17% of $GABA_A$ receptors in the rat. Subtype assemblies containing an α5 subunit are expressed predominantly in the hippocampus and cortex and are thought to represent about 4% of $GABA_A$ receptors in the rat.

A characteristic property of all known $GABA_A$ receptors is the presence of a number of modulatory sites, one of which is the benzodiazepine (BZ) binding site. The BZ binding site is the most explored of the $GABA_A$ receptor modulatory sites, and is the site through which anxiolytic drugs such as diazepam and temazepam exert their effect. Before the cloning of the $GABA_A$ receptor gene family, the benzodiazepine binding site was historically subdivided into two subtypes, BZ1 and BZ2, on the basis of radioligand binding studies. The BZ1 subtype has been shown to be pharmacologically equivalent to a $GABA_A$ receptor comprising the α1 subunit in combination with a β subunit and γ2. This is the most abundant $GABA_A$ receptor subtype, and is believed to represent almost half of all $GABA_A$ receptors in the brain.

Two other major populations are the γ2βγ2 and α3βγ2/3 subtypes. Together these constitute approximately a further 35% of the total $GABA_A$ receptor repertoire. Pharmacologically this combination appears to be equivalent to the BZ2 subtype as defined previously by radioligand binding, although the BZ2 subtype may also include certain α5-containing subtype assemblies. The physiological role of these subtypes has hitherto been unclear because no sufficiently selective agonists or antagonists were known.

It is now believed that agents acting as BZ agonists at $α1βγ2$, $α2βγ2$ or $α3βγ2$ subunits will possess desirable anxiolytic properties. Compounds which are modulators of the benzodiazepine binding site of the $GABA_A$ receptor by acting as BZ agonists are referred to hereinafter as "$GABA_A$ receptor agonists". The α1-selective $GABA_A$ receptor agonists alpidem and zolpidem are clinically prescribed as hypnotic agents, suggesting that at least some of the sedation associated with known anxiolytic drugs which act at the BZ1 binding site is mediated through $GABA_A$ receptors containing the α1 subunit. Accordingly, it is considered that $GABA_A$ receptor agonists which bind more effectively to the α2 and/or α3 subunit than to α1 will be effective in the treatment of anxiety with a reduced propensity to cause sedation. Also, agents which are antagonists or inverse agonists at α1 might be employed to reverse sedation or hypnosis caused by α1 agonists.

The compounds of the present invention, being selective ligands for $GABA_A$ receptors, are therefore of use in the treatment and/or prevention of a variety of disorders of the central nervous system. Such disorders include anxiety disorders, such as panic disorder with or without agoraphobia, agoraphobia without history of panic disorder, animal and other phobias including social phobias, obsessive-compulsive disorder, stress disorders including post-traumatic and acute stress disorder, and generalized or substance-induced anxiety disorder; neuroses; convulsions; migraine; and depressive or bipolar disorders, for example single-episode or recurrent major depressive disorder, dysthymic disorder, bipolar I and bipolar II manic disorders, and cyclothymic disorder.

In DE-A-2741763, and in U.S. Pat. Nos. 4,260,755, 4,260,756 and 4,654,343, are described various classes of 1,2,4-triazolo[4,3-b]pyridazine derivatives which are alleged to be useful as anxiolytic agents. The compounds described in DE-A-2741763 and in U.S. Pat. No. 4,260,755 and 4,654,343 possess a phenyl substituent at the 6-position of the triazolo-pyridazine ring system. The compounds described in U.S. Pat. No. 4,260,756, meanwhile, possess a heteroaryl moiety at the 6- or 8-position. In none of these publications, however, is there any disclosure or suggestion of 1,2,4-triazolo[4,3-b]pyridazine derivatives wherein the substituent at the 6-position is attached through a directly linked oxygen atom.

EP-A-0085840 and EP-A-0134946 describe related series of 1,2,4-triazolo[3,4-a]phthalazine derivatives which are stated to possess antianxiety activity. However, there is no disclosure nor any suggestion in either of these publications of replacing the benzo moiety of the triazolo-phthalazine ring system with any other functionality.

The present invention provides a class of triazolo-pyridazine derivatives which possess desirable binding properties at various $GABA_A$ receptor subtypes. The compounds in accordance with the present invention have good affinity as ligands for the α2 and/or α3 subunit of the human $GABA_A$ receptor. The compounds of this invention may display more effective binding to the α2 and/or α3 subunit than to the α1 subunit. Desirably, the compounds of the invention will exhibit functional selectivity in terms of a selective efficacy for the α2 and/or α3 subunit relative to the al subunit.

The compounds of the present invention are $GABA_A$ receptor subtype ligands having a binding affinity ($K_i$) for the α2 and/or α3 subunit, as measured in the assay described hereinbelow, of 100 nM or less, typically of 50 nM or less, and ideally of 10 nM or less. The compounds in accordance with this invention may possess at least a 2-fold, suitably at least a 5-fold, and advantageously at least a 10-fold, selective affinity for the α2 and/or α3 subunit relative to the al subunit. However, compounds which are unselective in terms of their binding affinity for the α2 and/or α3 subunit relative to the α1 subunit are also encompassed within the scope of the present invention; such compounds will desirably exhibit functional selectivity in terms of a selective efficacy for the α2 and/or α3 subunit relative to the α1 subunit.

A number of dementing illnesses such as Alzheimer's disease are characterised by a progressive deterioration in cognition in the sufferer. It would clearly be desirable to enhance cognition in subjects desirous of such treatment, for example for subjects suffering from a dementing illness.

It has been reported by McNamara and Skelton in Psychobiology, 21:101–108, that the benzodiazepine receptor inverse agonist β-CCM enhanced spatial learning in the Morris watermaze. However, β-CCM and other conventional benzodiazepine receptor inverse agonists are proconvulsant or convulsant which makes it clear that they cannot be used as cognition enhancing agents in humans.

However, we have now discovered that it is possible to obtain medicaments which have cognition enhancing effects which may be employed with less risk of proconvulsant effects previously described with benzodiazepine receptor partial or full inverse agonists.

It has now been discovered that use of an α5 receptor partial or full inverse agonist which is relatively free of activity at α1 and/or α2 and/or α3 receptor binding sites can be used to provide a medicament which is useful for enhancing cognition but in which proconvulsant activity is reduced or eliminated. Inverse agonists at α5 which are not free of activity at α1 and/or α2 and/or α3 but which are functionally selective for α5 can also be used. Inverse agonists which are both selective for α5 and are relatively free of activity at α1, α2 and α3 receptor binding sites are preferred.

European Patent Applications 0085840 and 0134946 describe related series of 1,2,4-triazolo[3,4-a]phthalazine derivatives which are stated to possess antianxiety activity. However, there is no disclosure nor any suggestion in either of these publications of the compounds of the present invention, nor that the compounds disclosed in the Applications have any cognition enhancing properties.

The present invention provides a compound of formula I, or a salt or prodrug thereof:

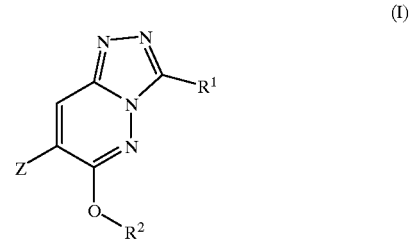

(I)

wherein

Z represents $C_{1-6}$ akyl, $C_{3-7}$ cycloalkyl, $C_{4-7}$ cycloalkenyl, aryl, $C_{3-7}$ heterocycloalkyl, heteroaryl or di($C_{1-6}$) alkylamino, any of which groups may be optionally substituted;

$R^1$ represents an optionally substituted five-membered heteroaromatic ring selected from oxazole, thiazole, isoxazole, isothiazole, imidazole, pyrazole, oxadiazole, thiadiazole, triazole and tetrazole; or $R^1$ represents an optionally substituted six-membered heteroaromatic ring selected from pyrazine, pyrimidine and pyridazine; and $R^2$ represents cyano($C_{1-6}$)alkyl, hydroxy($C_{1-6}$)alkyl, $C_{3-7}$ cycloalkyl($C_{1-6}$)alkyl, propargyl, $C_{3-7}$ heterocycloallylcarbonyl($C_{1-6}$)alkyl, aryl($C_{1-6}$)alkyl or heteroaryl($C_{1-6}$)alkyl, any of which groups may be optionally substituted.

The groups Z, $R^1$ and $R^2$ may be unsubstituted, or substituted by one or more, suitably by one or two, substituents. In general, the groups Z, $R^1$ and $R^2$ will be unsubstituted or monosubstituted. Examples of optional substituents on the groups Z, $R^1$ and $R^2$ include $C^{1-6}$ alkyl, aryl($C_{1-6}$)alkyl, pyridyl($C_{1-6}$)alkyl, halogen, halo($C_{1-6}$) alkyl, cyano, cyano($C_{1-6}$)alkyl, hydroxy, hydroxymethyl, $C^{1-6}$ alkoxy, $C_{3-7}$ cycloalyl($C_{1-6}$)alkoxy, $C_{3-7}$ cycloalkoxy, amino($C_{1-6}$)alkyl, di($C_{1-6}$)alkylamino($C_{1-6}$)alkyl, di($C_{1-6}$) alkylaminocarbonyl($C_{1-6}$)alkyl, N-($C_{1-6}$)alkylpiperidinyl, pyrrolidinyl($C_{1-6}$)alkyl, piperazinyl($C_{1-6}$)alkyl, morpholinyl ($C_{1-6}$)alkyl, di($C_{1-6}$)alkylmorpholinyl($C_{1-6}$)alkyl and imidazolyl($C_{1-6}$)alkyl.

As used herein, the expression "$C_{1-6}$ alkyl" includes methyl and ethyl groups, and straight-chained or branched propyl, butyl, pentyl and hexyl groups. Particular alkyl groups are methyl, ethyl, n-propyl, isopropyl, tert-butyl and 1,1-dimethylpropyl. Derived expressions such as "$C_{1-6}$ alkoxy" are to be construed accordingly.

Typical $C_{3-7}$ cycloalkyl groups include cyclopropyl, cyclobutyl, cyclopentyl and cyclohexyl.

The expression "$C_{3-7}$ cycloalkyl($C_{1-6}$)alkyl" as used herein includes cyclopropylmethyl, cyclobutylmethyl, cyclopentylmethyl and cyclohexylmethyl.

Typical $C_{4-7}$ cycloalkenyl groups include cyclobutenyl, cyclopentenyl and cyclohexenyl.

Typical aryl groups include phenyl and naphthyl, preferably phenyl.

The expression "aryl($C_{1-6}$)alkyl" as used herein includes benzyl, phenylethyl, phenylpropyl and naphthylmethyl.

Suitable heterocycloalkyl groups include azetidinyl, pyrrolidinyl, piperidinyl, piperazinyl, morpholinyl and thiomorpholinyl groups.

Suitable heteroaryl groups include pyridinyl, quinolinyl, isoquinolinyl, pyridazinyl, pyrimidinyl, pyrazinyl, quinoxalinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl groups.

The expression "heteroaryl($C_{1-6}$)alkyl" as used herein includes furylmethyl, furylethyl, thienylmethyl, thienylethyl, pyrazolylmethyl, oxazolylmethyl, oxazolylethyl, isoxazolylmethyl, thiazolylmethyl, thiazolylethyl, imidazolylmethyl, imidazolylethyl, benzimidazolylmethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyridazinylmethyl, pyrimidinylmethyl, pyrazinylmethyl, quinolinylmethyl, isoquinolinylmethyl and quinoxalinylmethyl.

The term "halogen" as used herein includes fluorine, chlorine, bromine and iodine, especially fluorine or chlorine.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixng a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Design of Prodrugs*, ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

Examples of suitable values for the substituent Z include methyl, ethyl, isopropyl, tert-butyl, 1,1-dimethylpropyl, methyl-cyclopropyl, cyclobutyl, methyl-cyclobutyl, cyclopentyl, methyl-cyclopentyl, cyclohexyl, cyclobutenyl, phenyl, pyrrolidinyl, methyl-pyrrolidinyl, piperidinyl, morpholinyl, thiomorpholinyl, pyridinyl, furyl, thienyl, chloro-thienyl and diethylamino. A particular value of Z is phenyl.

Suitable values for the moiety $R^1$ include thiazolyl, isoxazolyl and pyrazinyl, any of which groups may be optionally substituted by one or more substituents. Suitably $R^1$ is unsubstituted, or substituted by one or two substituents. In general, $R^1$ will be unsubstituted or monosubstituted. A particular substituent on the moiety $R^1$ is $C_{1-6}$ alkyl, especially methyl.

Particular values of $R^1$ include methylthiazolyl (especially 4-methyl-thiazol-2-yl), methylisoxazolyl (especially 5-methylisoxazol-3-yl) and pyrazinyl (especially pyrazin-2-yl).

Suitable values for the substituent $R^2$ in the compounds according to the invention include cyanomethyl, hydroxybutyl, cyclohexylmethyl, propargyl, pyrrolidinylcarbonylmethyl, benzyl, pyrazolylmethyl, isoxazolylmethyl, thiazolylmethyl, thiazolylethyl, imidazolylmethyl, benzimidazolylmethyl, oxadiazolylmethyl, triazolylmethyl, tetrazolylmethyl, pyridinylmethyl, pyridazinylmethyl, pyrimidinylmethyl, pyrazinylmethyl, quinolinylmethyl, isoquinolinylmethyl and quinoxalinylmethyl, any of which groups may be optionally substituted by one or more substituents. Typical values of $R^2$ include triazolylmethyl and pyridinylmethyl, either of which groups may be optionally substituted by one or more substituents.

Examples of suitable optional substituents on the group $R^2$ include $C_{1-6}$ alkyl, aryl($C_{1-6}$)alkyl, pyridyl($C_{1-6}$)alkyl, halogen, halo($C_{1-6}$)alkyl, cyano, cyano($C_{1-6}$)alkyl, hydroxymethyl, $C_{1-6}$ alkoxy, $C_{3-7}$ cycloalkyl($C_{1-6}$)alkoxy, amino($C_{1-6}$)alkyl, di($C_{1-6}$)alkylamino($C_{1-6}$)alkyl, di($C_{1-6}$)alkylaminocarbonyl($C_{1-6}$)alkyl, N-($C_{1-6}$)alkylpiperidinyl, pyrrolidinyl($C_{1-6}$)alkyl, piperazinyl($C_{1-6}$)alkyl, morpholinyl($C_{1-6}$)alkyl and di($C_{1-6}$)alkylmorpholinyl($C_{1-6}$)alkyl, especially $C_{1-6}$ alkyl.

Specific illustrations of particular substituents on the group $R^2$ include methyl, ethyl, n-propyl, benzyl, pyridinylmethyl, chloro, chloromethyl, cyano, cyanomethyl, hydroxymethyl, ethoxy, cyclopropylmethoxy, dimethylaminomethyl, aminoethyl, dimethylaminoethyl, dimethylaminocarbonylmethyl, N-methylpiperidinyl, pyrrolidinylethyl, piperazinylethyl, morpholinylmethyl and dimethylmorpholinylmethyl, especially methyl.

Representative values of $R^2$ include cyanomethyl, hydroxybutyl, hydroxymethyl-cyclohexylmethyl, propargyl, dimethylaminomethyl-propargyl, dimethylmorpholinylmethyl-propargyl, pyrrolidinylcarbonylmethyl, cyanobenzyl, hydroxymethyl-benzyl, pyrazolylmethyl, dimethyl-pyrazolylmethyl, methyl-isoxazolylmethyl, thiazolylmethyl, methyl-thiazolylmethyl, ethyl-thiazolylmethyl, methyl-thiazolylethyl, imidazolylmethyl methyl-imidazolylmethyl, ethyl-imidazolylmethyl, benzyl-imidazolylmethyl, benzimidazolylmethyl, methyl-oxadiazolylmethyl, triazolylmethyl, methyl-triazolylmethyl, propyl-triazolylmethyl, benzyl-triazolylmethyl, pyridinylmethyl-triazolylmethyl, cyanomethyl-triazolylmethyl, dimethylaminomethyl-triazolylmethyl, aminoethyl-triazolylmethyl, dimethylaminoethyl-triazolylmethyl, dimethylaminocarbonylmethyl-triazolylmethyl, N-methylpiperidinyl-triazolylmethyl, pyrrolidinylethyl-triazolylmethyl, piperazinylethyl-triazolylmethyl, morpholinylethyl-triazolylmethyl, methyl-tetrazolylmethyl, pyridinylmethyl, methyl-pyridinylmethyl, dimethyl-pyridinylmethyl, ethoxy-pyridinylmethyl, cyclopropylmethoxy-pyridinylmethyl, pyridazinylmethyl, chloro-pyridazinylmethyl, pyrimidinylmethyl, pyrazinylmethyl, quinolinylmethyl, isoquinolinylmethyl and quinoxalinylmethyl.

Particular values of $R^2$ include triazolylmethyl, methyl-triazolylmethyl and pyridinylmethyl.

A particular sub-class of compounds according to the invention is represented by the compounds of formula IIA, and salts and prodrugs thereof:

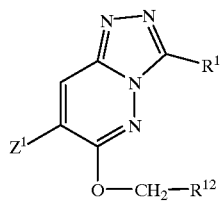

(IIA)

wherein R¹ is as defined above;

Z¹ represents $C_{1-6}$ alkyl, $C_{3-7}$ cycloalkyl or aryl; and

R¹² represents optionally substituted heteroaryl.

Examples of optional substituents on the group R¹² suitably include $C_{1-6}$ alkyl, especially methyl.

Particular values of R¹² include triazolyl, methyltriazolyl and pyridinyl.

Particular values of Z¹ include tert-butyl, cyclobutyl, cyclopentyl and phenyl, especially phenyl.

Specific compounds within the scope of the present invention include:

6-(1-methyl-1H-1,2,4-triazol-3-ylmethyloxy)-7-phenyl-3-(pyrazin-2-yl)-1,2,4-triazolo[4,3-b]pyridazine;

6-(2-methyl-2H-1,2,4-triazol-3-ylmethyloxy)-7-phenyl-3-(pyrazin-2-yl)-1,2,4-triazolo[4,3-b]pyridazine;

7-phenyl-3-(pyrazin-2-yl)-6-(1H-1,2,4-triazol-3-ylmethyloxy)-1,2,4-triazolo[4,3-b]pyridazine;

3-(4-methylthiazol-2-yl)-7-phenyl-6-(pyridin-2-ylmethyloxy)-1,2,4-triazolo[4,3-b]pyridazine;

and salts and prodrugs thereof.

A further particular sub-class of compounds according to the invention is represented by the compounds of formula IIB, and salts and prodrugs thereof:

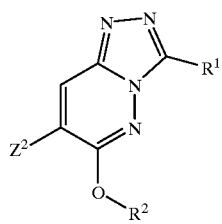

(IIB)

wherein:

R¹ and R² are as defined above; and

Z² is pyridyl, tertiary butyl, cyclobutyl or methylcyclobutyl.

With respect to compounds of formula (IIB), R¹ is preferably an optionally substituted five-membered heteroaromatic ring selected from oxazole, thiazole, isoxazole, isothiazole, imidazole, pyrazole, oxadiazole, thiadiazole, triazole and tetrazole wherein the optional substituents are selected from $C_{1-6}$alkyl, $C_{1-6}$alkoxy, halogen, halo($C_{1-6}$) alkyl, hydroxy, $C_{3-7}$cycloalkyl and $C_{3-7}$cycloalkoxy. Preferably the optional substituents are selected from $C_{1-6}$alkyl, $C_{1-6}$alkoxy and halogen and more preferably selected from methyl and chloro, especially methyl.

Preferably R¹ is unsubstituted or monosubstituted and more preferably monosubstituted.

R¹ is most preferably an optionally substituted isoxazole or oxadiazole such as an isoxazol-3-yl or a 1,2,4-oxadiazol-3-yl. R¹ is thus preferably a methylisoxazole, isoxazole, chloroisoxazole or methyloxadiazole, particularly a 5-methylisoxazol-3-yl, 5-chloroisoxazol-3-yl, isoxazol-3-yl or 5-methyl-1,2,4-oxadiazol-3-yl group. R¹ may also be 5-ethoxyisoxazol-3-yl.

With respect to compounds of formula (IIB), R² is preferably a heteroaryl($C_{1-6}$)alkyl. The heteroaryl group is preferably a 5-membered heteroaromatic ring containing 1, 2, 3 or 4 heteroatoms independently chosen from oxygen, nitrogen and sulphur, at most one of the heteroatoms being oxygen or sulphur, or a 6-membered heteroaromatic ring containing 1, 2, or 3 nitrogen atoms, the heteroaromatic ring being optionally substituted by one, two or three groups independently chosen from $C_{1-6}$alkyl, $C_{1-6}$alkoxy, halogen, phenyl$C_{1-6}$alkyl, amino and hydroxy.

When R² is pyridyl it may be in the form of the N-oxide.

R² is preferably a pyridine, triazole or imidazole.

When R² is substituted it is preferably monosubstituted.

Preferred substituents on R² are $C_{1-6}$alkyl groups such as methyl. Thus monosubstitution by methyl (especially when R² is a five-membered heteroaromatic ring) is favoured. When R² is a six-membered heteroaromatic ring it is preferably unsubstituted.

Particular examples of R² are pyrid-2-yl, 1-methyl-1,2,3-triazol-4-yl, 1-benzylimidazol-2-yl, 2-methyl-1,2,4-triazol-3-yl, 1-methyl-1,2,4-triazol-3-yl and 3-methyl-1,2,3-triazol-4-yl.

Other examples are 1-methyl-1,2,3-triazol-4-yl and 1-methyl-1,2,3-triazol-5-yl.

Z² may be tertiary butyl, cyclobutyl or methylcyclobutyl. When Z² is pyridyl it is preferably pyrid-4-yl.

Thus a preferred subclass of compounds of formula (IIB) is wherein:

Z² is as defined above;

R¹ is isoxazole or oxadiazole optionally substituted by chlorine or methyl; and

R² is pyridine; or imidazole or a triazole optionally substituted by methyl or benzyl and preferably substituted by methyl.

When Z² is a methylcyclobutyl group, 1-methylcyclobutyl is particularly preferred. In particular, Z² is preferably a tertiary butyl group.

Specific compounds within the scope of this subclass include:

7-t-butyl-3-(5-methylisoxazol-3-yl)-6-(2-pyridylmethyloxy)-1,2,4-triazolo[4,3-b]pyridazine;

7-t-butyl-3-(5-methylisoxazol-3-yl)-6-(1-methyl-1,2,4-triazol-3-yl)methyloxy-1,2,4-triazolo[4,3-b]pyridazine; and 7-t-butyl-3-(5-methylisoxazol-3-yl)-6-(1-methyl-1,2,3-triazol-4-yl)methyloxy-1,2,4-triazolo[4,3-b]pyridazine; and salts and prodrugs thereof.

Further specific compounds within the scope of this subclass include:

7-t-butyl-3-(5-methylisoxazol-3-yl)-6-(1-benzylimidazol-2-yl)methyloxy-1,2,4-triazolo[4,3-b]pyridazine;

7-t-butyl-3-(5-methylisoxazol-3-yl)-6-(2-methyl-1,2,4-triazol-3-yl)methyloxy 1,2,4-triazolo[4,3-b]pyridazine;

7-t-butyl-3-isoxazol-3-yl-6-(2-methyl-1,2,4-triazol-3-yl)methyloxy-1,2,4-triazolo[4,3-b]pyridazine;

7-t-butyl-3-isoxazol-3-yl-6-(1-methyl-1,2,4-triazol-4-yl)methyloxy-1,2,4-triazolo[4,3-b]pyridazine;

7-t-butyl-3-isoxazol-3-yl-6-(1-methyl-1,2,4-triazol-3-yl)methyloxy-1,2,4-triazolo[4,3-b]pyridazine;

7-t-butyl-3-isoxazol-3-yl-6-(3-methyl-1,2,3-triazol-4-yl)methyloxy-1,2,4-triazolo[4,3-b]pyridazine;

7-t-butyl-3-(5-chloroisoxazol-3-yl)-6-(2-methyl-1,2,4-triazol-3-yl)methyloxy-1,2,4-triazolo[4,3-b]pyridazine;

7-c-butyl-3-(5-methylisoxazol-3-yl)-6-(1-methyl-1,2,4-triazol-3-yl)methyloxy-1,2,4-triazolo[4,3-b]pyridazine;

7-c-butyl-3-(5-methylisoxazol-3-yl)-6-(2-methyl-1,2,4-triazol-3-yl)methyloxy-1,2,4-triazolo[4,3-b]pyridazine;

7-(1-methylcyclobutyl)-3-isoxazol-3-yl-6-(1-methyl-1,2,3-triazol-4-yl)methyloxy-1,2,4-triazolo[4,3-b]pyridazine;

7-(1-methylcyclobutyl)-3-(5-methylisoxazol-3-yl)-6-(1-methyl-1,2,3-triazol-4-yl)methyloxy-1,2,4-triazolo[4,3-b]pyridazine;

7-(1-methylcyclobutyl)-3-(5-methylisoxazol-3-yl)-6-(2-methyl-1,2,4-triazol-3-yl)methyloxy-1,2,4-triazolo[4,3-b]pyridazine;

7-t-butyl-3-(5-methyl-1,2,4-oxadiazol-3-yl)-6-(2-methyl-1,2,4-triazol-3-yl)methyloxy-1,2,4-triazolo[4,3-b]pyridazine;

7-t-butyl-3-(5-methyl-1,2,4-oxadiazol-3-yl)-6-(1-methyl-1,2,4-triazol-3-yl)methyloxy-1,2,4-triazolo[4,3-b]pyridazine; and 7-t-butyl-3-(5-methyl-1,2,4-oxadiazol-3-yl)-6-(1-methyl-1,2,3-triazol-4-yl)methyloxy-1,2,4-triazolo[4,3-b]pyridazine; and salts and prodrugs thereof Yet further specific compounds within the scope of this subclass include:

7-(1-methylcyclobutyl)-3-(5-methylisoxazol-3-yl)-6-(1-methyl-1,2,4-triazol-3-yl)methyloxy-1,2,4-triazolo[4,3-b]pyridazine;

7-(1-methylcyclobutyl)-3-(5-methylisoxazol-3-yl)-6-(1-benzyl imidazol-2-yl)methyloxy-1,2,4-triazolo[4,3-b]pyridazine;

7-(1-methylcyclobutyl)-3-(5-chloroisoxazol-3-yl)-6-(1-methyl-1,2,3-triazol-5-yl)methyloxy-1,2,4-triazolo[4,3-b]pyridazine;

7-(1-methylcyclobutyl)-3-(5-chloroisoxazol-3-yl)-6-(1-methyl-1,2,3-triazol-4-yl)methyloxy-1,2,4-triazolo[4,3-b]pyridazine;

7-(1-methylcyclobutyl)-3-(5-chloroisoxazol-3-yl)-6-(2-methyl-1,2,4-triazol-3-yl)methyloxy-1,2,4-triazolo[4,3-b]pyridazine;

7-(1-methylcyclobutyl)-3-(5-chloroisoxazol-3-yl)-6-(1-methyl-1,2,4-triazol-3-yl)methyloxy-1,2,4-triazolo[4,3-b]pyridazine;

7-(1-methylcyclobutyl)-3-(5-chloroisoxazol-3-yl)-6-(1-benzylimidazol-2-yl)methyloxy-1,2,4-triazolo[4,3-b]pyridazine;

7-t-butyl-3-(5-ethoxyisoxazol-3-yl)-6-(1-methyl-1,2,3-triazol-5-yl)methyloxy-1,2,4-triazolo[4,3-b]pyridazine;

7-t-butyl-3-(5-ethoxyisoxazol-3-yl)-6-(1-methyl-1,2,3-triazol-4-yl)methyloxy-1,2,4-triazolo[4,3-b]pyridazine;

7-t-butyl-3-(5-ethoxyisoxazol-3-yl)-6-(1-methyl-1,2,4-triazol-3-yl)methyloxy-1,2,4-triazolo[4,3-b]pyridazine;

7-t-butyl-3-(5-ethoxyisoxazol-3-yl)-6-(1-benzylimidazol-2-yl)methyloxy-1,2,4-triazolo[4,3-b]pyridazine;

7-t-butyl-3-(5-chloroisoxazol-3-yl)-6-(1-methyl-1,2,3-triazol-5-yl)methyloxy)-1,2,4-triazolo[4,3-b]pyridazine;

7-t-butyl-3-(5-chloroisoxazol-3-yl)-6-(1-methyl-1,2,3-triazol-4-yl)methyloxy)-1,2,4-triazolo[4,3-b]pyridazine;

7-t-butyl-3-(5-chloroisoxazol-3-yl)-6-(1-benzylimidazol-2-yl)methyloxy-1,2,4-triazolo[4,3-b]pyridazine;

7-pyrid-4-yl-3-(5-methylisoxazol-3-yl)-6-(2-methyl-1,2,4-triazol-3-yl)methyloxy-1,2,4-triazolo[4,3-b]pyridazine;

7-pyrid-3-yl-3-(5-methylisoxazol-3-yl)-6-(2-methyl-1,2,4-triazol-3-yl)methyloxy-1,2,4-triazolo[4,3-b]pyridazine;

7-pyrid-2-yl-3-(5-methylisoxazol-3-yl)-6-(2-methyl-1,2,4-triazol-3-yl)methyloxy-1,2,4-triazolo[4,3-b]pyridazine;

7-pyrid-4-yl-3-(5-methylisoxazol-3-yl)-6-(1-methyl-1,2,3-triazol-5-yl)methyloxy-1,2,4-triazolo[4,3-b]pyridazine;

7-pyrid-3-yl-3-(5-methylisoxazol-3-yl)-6-(1-methyl-1,2,3-triazol-5-yl)methyloxy-1,2,4-triazolo[4,3-b]pyridazine;

7-pyrid-2-yl-3-(5-methylisoxazol-3-yl)-6-(1-methyl-1,2,3-triazol-5-yl)methyloxy-1,2,4-triazolo[4,3-b]pyridazine;

7-pyrid-4-yl-3-(5-methylisoxazol-3-yl)-6-(1-methyl-1,2,4-triazol-3-yl)methyloxy-1,2,4-triazolo[4,3-b]pyridazine;

7-pyrid-3-yl-3-(5-methylisoxazol-3-yl)-6-(1-methyl-1,2,4-triazol-3-yl)methyloxy-1,2,4-triazolo[4,3-b]pyridazine;

7-pyrid-2-yl-3-(5-methylisoxazol-3-yl)-6-(1-methyl-1,2,4-triazol-3-yl)methyloxy-1,2,4-triazolo[4,3-b]pyridazine;

7-pyrid-4-yl-3-(5-methylisoxazol-3-yl)-6-(1-methyl-1,2,4-triazol-4-yl)methyloxy-1,2,4-triazolo[4,3-b]pyridazine; and 7-pyrid-3-yl-3-(5-methylisoxazol-3-yl)-6-(1-methyl-1,2,3-triazol-4-yl)methyloxy-1,2,4-triazolo[4,3-b]pyridazine; and salts and prodrugs thereof Also provided by the present invention is a method for the treatment and/or prevention of anxiety which comprises administering to a patient in need of such treatment an effective amount of a compound of formula I as defined above or a pharmaceutically acceptable salt thereof or a prodrug thereof.

Further provided by the present invention is a method for the treatment and/or prevention of convulsions (e.g. in a patient suffering from epilepsy or a related disorder) which comprises administering to a patient in need of such treatment an effective amount of a compound of formula I as defined above or a pharmaceutically acceptable salt thereof or a prodrug thereof.

The binding affinity ($K_i$) of the compounds according to the present invention for the α3 subunit of the human $GABA_A$ receptor is conveniently as measured in the assay described hereinbelow. The α3 subunit binding affinity ($K_i$) of compounds according to the invention is ideally 10 nM or less, preferably 2 nM or less, and more preferably 1 nM or less.

The compounds according to the present invention will ideally elicit at least a 40%, preferably at least a 50%, and more preferably at least a 60%, potentiation of the GABA $EC_{20}$ response in stably transfected recombinant cell lines expressing the α3 subunit of the human $GABA_A$ receptor. Moreover, the compounds of the invention will ideally elicit at most a 30%, preferably at most a 20%, and more preferably at most a 10%, potentiation of the GABA $EC_{20}$ response in stably transfected recombinant cell lines expressing the α1 subunit of the human $GABA_A$ receptor.

The potentiation of the GABA $EC_{20}$ response in stably transfected cell lines expressing the α3 and α1 subunits of the human $GABA_A$ receptor can conveniently be measured by procedures analogous to the protocol described in Wafford et al., *Mol. Pharmacol.*, 1996, 50, 670–678. The procedure will suitably be carried out utilising cultures of stably transfected eukaryotic cells, typically of stably transfected mouse Ltk⁻ fibroblast cells.

The compounds according to the present invention exhibit anxiolytic activity, as demonstrated by a positive response in the elevated plus maze and conditioned suppression of drinking tests (cf. Dawson et al., *Psychopharmacology*, 1995, 121, 109–117). Moreover, the compounds of the invention are substantially non-sedating, as confirmed by an appropriate result obtained from the response sensitivity (chain-pulling) test (cf. Bayley et al., *J. Psychopharmacol.*, 1996, 10, 206–213).

The compounds according to the present invention also exhibit anticonvulsant activity. This is demonstrated by their ability to block pentylenetetrazole-induced seizures in rats and mice, following a protocol analogous to that described by Bristow et al. in *J. Pharmacol. Exp. Ther.*, 1996, 279, 492–501.

In order to elicit their behavioural effects, the compounds of the invention will be brain-penetrant; in other words, these compounds will be capable of crossing the so-called "blood-brain barrier". Preferably, the compounds of the invention will be capable of exerting their beneficial therapeutic action following administration by the oral route.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of anxiety, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds of the present invention have a good binding affinity ($K_i$) for the α5 subunit. In a preferred embodiment the compounds of the invention are binding selective for the α5 subunit relative to the α1, α2 and α3 subunits. In another preferred embodiment the compounds are functionally selective for the α5 subunit as partial or full inverse agonists whilst substantially being antagonists at the α1, α2 and α3 subunits. In particular the compounds of formula IIB are generally inverse agonists of the α5 subunit.

Cognition enhancement can be shown by testing the compounds in the Morris watermaze as reported by McNamara and Skelton, Psychobiology, 21:101–108. The functional efficacy at the various receptor subtypes can be calculated using the method disclosed in WO-A-9625948.

The present invention also provides a compound of the invention for use in a method of treatment of the human body. Preferably the treatment is for a condition associated with $GABA_A$ receptors comprising the α5 subunit and/or for the enhancement of cognition. Preferably the condition is a neurological deficit with an associated cognitive disorder such as. a dementing illness such as Alzheimer's disease. Other conditions to be treated include cognition deficits due to traumatic injury, stroke, Parkinson's disease, Downs syndrome, age related memory deficits, attention deficit disorder and the like.

Thus, for example, the compounds of the present invention can be used in a variety of disorders of the central nervous system. Such disorders include delirium, dementia and amnestic and other cognitive disorders. Examples of delirium are delirium due to substance intoxication or substance withdrawal, delirium due to multiple etiologies and delirium NOS (not otherwise specified). Examples of dementia are: dementia of the Alzheimer's type with early onset which can be uncomplicated or with delirium, delusions or depressed mood; dementia of the Alzheimer's type, with late onset, which can be uncomplicated or with delirium, delusions or depressed mood; vascular dementia which can be uncomplicated or with delirium, delusions or depressed mood; dementia due to HIV disease; dementia due to head trauma; dementia due to Parkinson's disease; dementia due to Huntington's disease; dementia due to Pick's disease; dementia due to Creutzfeld-Jakob disease; dementia which is substance-induced persisting or due to multiple etiologies; and dementia NOS. Examples of amnestic disorders are amnestic disorder due to a particular medical condition or which is substance-induced persisting or which is amnestic disorder NOS.

Those compounds which are not inverse agonists at the α5 subtype may be used as alcohol antagonists or to treat obesity.

The present invention further provides the use of a compound of the present invention in the manufacture of a medicament for the enhancement of cognition, preferably in a human suffering from a dementing illness such as Alzheimer's disease.

Also disclosed is a method of treatment of a subject suffering from a cognition deficit, such as that resulting from a dementing illness such as Alzheimer's disease, which comprises administering to that subject an effective amount of a compound according to the present invention.

For the enhancement of cognition, a suitable dosage level is about 0.01 to 250 mg/kg per day, preferably about 0.01 to 100 mg/kg per day, and especially about 0.01 to 5 mg/kg of body weight per day. The compounds may be administered on a regimen of 1 to 4 times per day. In some cases, however, dosage outside these limits may be used.

It is preferred that the compounds of the present invention are ground, for example using a pestle and mortar or industrial equivalent thereto, to a particle size of between 1 and 10 μM, and preferably less than 5 μM, before formulation. The compounds may be micronised or sonicised by methods known in the art or nanonised, for example by methods disclosed in U.S. Pat. No. 5145684.

The compounds in accordance with the present invention may be prepared by a process which comprises reacting a compound of formula III with a compound of formula IV:

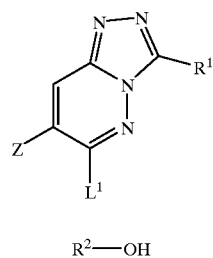

(III)

R²—OH (IV)

wherein Z, R¹ and R² are as defined above; and L¹ represents a suitable leaving group.

The leaving group L¹ is typically a halogen atom, especially chloro.

The reaction between compounds III and IV is conveniently effected by stirring the reactants in a suitable solvent, typically N,N-dimethyl-formamide, in the presence of a strong base such as sodium hydride or lithium bis(trimethylsilyl)amide.

The intermediates of formula III above may be prepared by reacting a compound of formula V with a substantially equimolar amount of a hydrazine derivative of formula VI:

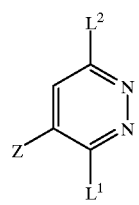

(V)

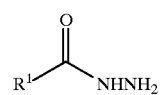

(VI)

wherein Z, R¹ and L¹ are as defined above, and L² represents a suitable leaving group; followed, if necessary, by separation of the resulting mixture of isomers by conventional means.

The leaving group L² is typically a halogen atom, especially chloro. In the intermediates of formula V, the leaving groups L¹ and L² may be the same or different, but are suitably the 'same, preferably both chloro.

The reaction between compounds V and VI is conveniently effected by heating the reactants in the presence of a base such as triethylamine, typically at reflux in an inert solvent such as xylene or 1,4-dioxane.

The reaction between compounds V and VI will, as indicated above, usually give rise to a mixture of isomeric products depending upon whether the hydrazine derivative VI displaces the leaving group L¹ or L². Thus, in addition to the required product of formula III, the isomeric compound wherein the Z moiety is in the adjacent position will usually be obtained to some extent. For this reason it will generally be necessary to separate the resulting mixture of isomers by conventional methods such as chromatography.

In another procedure, the compounds according to the invention may be prepared by a process which comprises reacting a compound of formula VII with a compound of formula VIII:

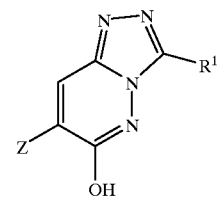

(VII)

R²—L³ (VIII)

wherein Z, R¹ and R² are as defined above; and L³ represents a suitable leaving group.

The leaving group L³ is suitably a halogen atom, typically chloro or bromo.

The reaction between compounds VII and VIII is conveniently effected by stirring the reactants in a suitable solvent, typically N,N-dimethylformamide, in the presence of a strong base such as sodium hydride.

The intermediates of formula VII above may conveniently be prepared by reacting a compound of formula III as defined above with an alkali metal hydroxide, e.g. sodium hydroxide. The reaction is conveniently effected in an inert solvent such as aqueous 1,4-dioxane, ideally at the reflux temperature of the solvent.

In a further procedure, the compounds according to the invention may be prepared by a process which comprises reacting a compound of formula Z-CO₂H with a compound of formula IX:

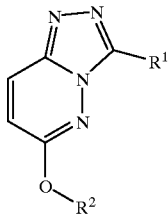

(IX)

wherein Z, R¹ and R² are as defined above; in the presence of silver nitrate and ammonium persulphate.

The reaction is conveniently carried out under acidic conditions in a suitable solvent, for example using sulphuric acid in aqueous acetonitrile, typically at an elevated temperature, e.g. the reflux temperature of the solvent.

The intermediates of formula IX correspond to the compounds of formula I as defined above wherein Z is hydrogen, and they may therefore be prepared by methods analogous to those described above for preparing the corresponding compounds of formula I.

The intermediates of formula V above may suitably be prepared by reacting a compound of formula Z-CO₂H with a compound of formula X:

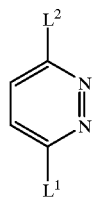

(X)

wherein L¹ and L² are as defined above; using procedures analogous to that described above for the reaction between the compound of formula Z-CO₂H and compound IX.

In a still further procedure, the compounds of formula I as defined above may be prepared by a process which comprises reacting a compound of formula XI with a compound of formula XII:

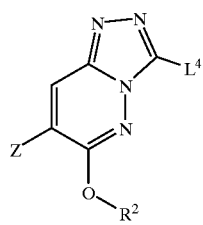

(XI)

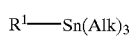

(XII)

wherein Z, R¹ and R² are as defined above, Alk represents a C$_{1-6}$ alkyl group, typically n-butyl, and L⁴ represents a suitable leaving group; in the presence of a transition metal catalyst.

The leaving group L⁴ is suitably a halogen atom, e.g. bromo.

A suitable transition metal catalyst of use in the reaction between compounds XI and XII comprises dichlorobis(triphenylphosphine)-palladium(II).

The reaction between compounds M and XII is conveniently effected in an inert solvent such as N,N-dimethylformamide, typically at an elevated temperature.

The intermediates of formula XI may be prepared by reacting a compound of formula IV as defined above with a compound of formula XIII:

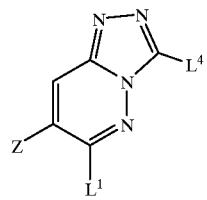

(XIII)

wherein Z, L¹ and L⁴ are as defined above; under conditions analogous to those described above for the reaction between compounds III and IV.

Where they are not commercially available, the starting materials of formula IV, VI, VIII, X, XII and XIII may be prepared by methods analogous to those described in the accompanying Examples, or by standard methods well known from the art.

According to yet further alternative methodology, intermediates of formula (III) may be prepared by reacting a compound of formula (XIV) with a compound of formula (XV):

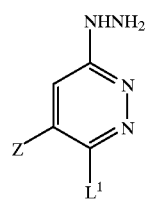

(XIV)

(XV)

wherein Z, L¹ and R¹ are as defined above, and W represents a suitable leaving group such as C$_{1-6}$alkoxy, chlorine or hydroxy.

The reaction is advantageously conducted in an inert organic solvent, generally in the presence of an organic nitrogen base and preferably under an inert atmosphere such as nitrogen. Suitable solvents include xylene, dioxane, tetrahydrofuran and lower aliphatic halogenated and aromatic hydrocarbons. Suitable organic nitrogen bases that may be employed include trialkylamines and pyridine. The reaction is generally conducted at a temperature range of from −20° C. to the reflux temperature of the reaction mixture, for a period of time that depends on the reactants employed and the temperature at which the reaction is carried out. The compound of formula (XV) may be activated by reacting with a compound such as bis-(2-oxo-3-oxazolidinyl) phosphinic chloride or 1,1'-dicarbonyldiimidazole before reaction with the hydrazine.

Alternatively, intermediates of formula (III) in which R¹ is an unsubstituted isoxazol-3-yl group or an isoxazol-3-yl group substituted by methyl, chloro or ethoxy, may be prepared from a chloroxime of formula (XVI):

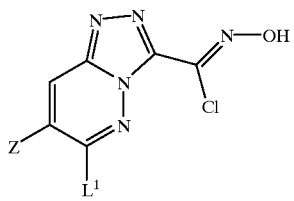

(XVI)

by reaction with an appropriate unsaturated compound to effect a cyclisation reaction. Generally, the reaction is effected in the presence of a base such as triethylamine in a suitable solvent such as dichloromethane.

Thus, for instance, where $R^1$ is a 5-methylisoxazol-3-yl group, a compound of formula (XVI) is reacted with 2-acetoxypropene; or 2-(tert-butyldimethylsilyloxy) propene; or propyne. Where $R^1$ is an unsubstituted isoxazol-3-yl group, vinyl acetate in xylene at reflux may be used. Where $R^1$ is a 5-chloroisoxazol-3-yl group, vinylidine chloride may be used. Where $R^1$ is a 5-ethoxyisoxazol-3-yl group, ethyl ethynyl ether may be used. Other substituents on the isoxazolyl group may be incorporated in an analogous manner.

Compounds of formula (XVI) are conveniently prepared from the corresponding oxime by a chlorination reaction using, for example, N-chlorosuccinimide in a solvent such as DMF.

The oxime may be prepared in a two-step reaction from a compound of formula (XIV) by reaction with dichloroacetic acid in a solvent such a toluene at reflux, followed by reaction with hydroxylamine hydrochloride in the presence of an acid such as trifluoroacetic acid at reflux.

Compounds of formula (XIV) may be prepared from a compound of formula (V) by reaction with hydrazine monohydrate in a solvent such as ethanol at reflux.

In an alternative procedure, intermediates of formula (III) in which $R^1$ is 1,2,4-oxadiazolyl group may be prepared in an analogous manner to that previously described for the isoxazolyl derivatives, using a compound of formula (XVII):

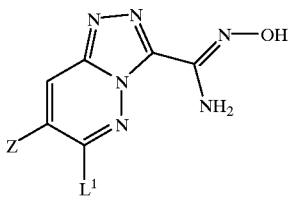

(XVII)

Thus, for example, to prepare a compound of formula (III) wherein $R^1$ is a 5-methyl-1,2,4-oxadiazol-3-yl group, a compound of formula (XVII) may be reacted with acetyl chloride in pyridine or by heating with acetic acid at reflux. Other substituents on the oxadiazolyl group may be incorporated using an appropriate acyl chloride or an appropriate acid, or by other methods well known to a person skilled in the art.

Compounds of formula (XVII) may be prepared by reaction of a compound of formula (XVI) with ammonium hydroxide in a solvent such as ethanol.

Where they are not commercially available, compounds of formula (XV) may be prepared by methods analogous to those described in the accompanying Examples, or by standard methods well known in the art.

It will be understood that any compound of formula I initially obtained from any of the above processes may, where appropriate, subsequently be elaborated into a further compound of formula I by techniques known from the art. For example, a compound of formula I initially obtained wherein $R^2$ is unsubstituted may be converted into a corresponding compound wherein $R^2$ is substituted, typically by standard alkylation procedures, for example by treatment with a haloalkyl derivative in the presence of sodium hydride and N,N-dimethylformamide, or with a hydroxyalkyl derivative in the presence of triphenylphosphine and diethyl azodicarboxylate. Furthermore, a compound of formula I initially obtained wherein $R^2$ represents cyano$(C_{1-6})$ alkyl may be converted into the corresponding 3-substituted 1,2,4-triazol-5-yl$(C_{1-6})$alkyl analogue by treatment with the appropriate acyl hydrazine derivative in the presence of a base such as sodium methoxide. Similarly, a compound of formula I initially obtained wherein $R^2$ represents an optionally substituted propargyl moiety may be converted into the corresponding 1,2,3-triazolylmethyl analogue by treatment with azide anion. A compound of formula I initially obtained wherein the $R^2$ substituent is substituted by a halogen atom, e.g. chloro, may be converted into the corresponding compound wherein the $R^2$ substituent is substituted by a di$(C_{1-6})$alkylamino moiety by treatment with the appropriate di$(C_{1-6})$alkylamine, typically with heating in a solvent such as 1,4-dioxane in a sealed tube.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds in accordance with this invention potently inhibit the binding of [$^3$H]-flumazenil to the benzodiazepine binding site of human GABA$_A$ receptors containing the α2 or α3 subunit stably expressed in Ltk cells.

Reagents

Phosphate buffered saline (PBS).

Assay buffer: 10 mM KH$_2$PO$_4$, 100 mM KCl, pH 7.4 at room temperature.

[$^3$H]-Flumazenil (18 nM for α1β3γ2 cells; 18 nM for α2β3γ2 cells; 10 nM for α3β3γ2 cells) in assay buffer.

Flunitrazepam 100 μM in assay buffer.

Cells resuspended in assay buffer (1 tray to 10 ml).

Harvesting Cells

Supernatant is removed from cells. PBS (approximately 20 ml) is added. The cells are scraped and placed in a 50 ml centrifuge tube. The procedure is repeated with a further 10 ml of PBS to ensure that most of the cells are removed. The cells are pelleted by centrifuging for 20 min at 3000 rpm in a benchtop centrifuge, and then frozen if desired. The pellets are resuspended in 10 ml of buffer per tray (25 cm×25 cm) of cells.

Assay

Can be carried out in deep 96-well plates or in tubes. Each tube contains:

300 μl of assay buffer.

50 μl of [$^3$H]-flumazenil (final concentration for α1β3γ2: 1.8 nM; for α2β3γ2: 1.8 nM; for α3β3γ2: 1.0 nM).

50 μl of buffer or solvent carrier (e.g. 10% DMSO) if compounds are dissolved in 10% DMSO (total); test compound or flunitrazepam (to determine non-specific binding), 10 μM final concentration.

100 μl of cells.

Assays are incubated for 1 hour at 40° C., then filtered using either a Tomtec or Brandel cell harvester onto GF/B filters followed by 3×3 ml washes with ice cold assay buffer. Filters are dried and counted by liquid scintillation counting. Expected values for total binding are 3000–4000 dpm for total counts and less than 200 dpm for non-specific binding if using liquid scintillation counting, or 1500–2000 dpm for total counts and less than 200 dpm for non-specific binding if counting with meltilex solid scintillant. Binding parameters are determined by non-linear least squares regression analysis, from which the inhibition constant $K_i$ can be calculated for each test compound.

The compounds of the accompanying Examples were tested in the above assay, and all were found to possess a $K_i$ value for displacement of [$^3$H]-flumazenil from the α2 and/or α3 subunit of the human GABA$_A$ receptor of 100 nM or less.

Further, compounds of Examples 5–7 were tested in the above assay for binding to the α5 subunit (10 nM for α5β3γ2 cells used as reagent giving a final concentration of 1.0 nM) and were found to possess a $K_i$ value for the α5 subunit of 100 nM or less.

EXAMPLE 1

6-(1-Methyl-1H-1,2,4-triazol-3-ylmethoxy)-7-phenyl-3-(pyrazin-2-yl)-1,2,4-triazolo[4,3-b]pyridazine a) 4-Phenylpyridazine-3,6-dione Phenylmaleic anhydride (20 g, 115 mmol), sodium acetate trihydrate (1875 g, 138 mmol), hydrazine monohydrate (6.68 ml, 133 mmol) and 40% aqueous acetic acid (400 ml) were heated at reflux for 15 h then allowed to cool. The reaction mixture was left to cool in the fridge for 1 h. The solid produced was filtered and washed with water and diethyl ether before drying in a vacuum oven at 40° C. to give the required product (7.26 g). 1H NMR (250 MHz, DMSO) δ 3.43 (2H, broad peak), 7.17 (1H, s), 7.44 (3H, m), 7.81 (2H, m); MS (ES$^+$) m/e 189 [MH$^+$].

b) 3,6-Dichloro-4-phenylpyridazine

The product from Example 1 step a) (7.26 g, 38 mmol) was dissolved in phosphorus oxychloride (145 ml, 155 mmol) and heated under reflux for 5.5 h. The solvent was removed under vacuum and the residue azeotroped with toluene (2×50 ml). The residue was dissolved in dichloromethane (200 ml) and the solution was neutralised by the addition of solid and aqueous sodium hydrogen carbonate (cautiously). When the effervescence had ceased, the organic layer was separated and the aqueous layer extracted with dichloromethane (2×200 ml). The combined organic layers were dried (MgSO$_4$), filtered and evaporated to give the required product (8.92 g). $^1$H NMR (250 MHz, DMSO) δ 7.54 (5H, m), 8.14 (1H, s); MS (ES$^+$) m/e 225 [MH$^+$].

c) Methyl 2-pyrazine carboxylate

Acetyl chloride (50 ml) was added very slowly to methanol (500 ml), and the mixture was allowed to cool before pyrazine-2-carboxylic acid (15 g, 124 mmol) in methanol (15 ml) was added. The reaction mixture was left to stand at room temperature overnight. The methanol was removed in vacuo to give the required product (22 g). $^1$H NMR (250 MHz, DMSO) δ 3.95 (3H, s), 8.82 (1H, m), 8.90 (1H, d, J=2.5 Hz), 9.21 (1H, d, J=2.5 Hz); MS (ES$^+$) m/e 153 [MH$^+$].

d) Pyrazine-2-hydrazide

To a solution of the product from Example 1 step c) (22 g, 159 mmol) in methanol (250 ml) was slowly added hydrazine monhydrate (36.6 ml, 710 mmol). The reaction mixture was stirred for 1.5 h. The precipitate produced was filtered, washed with diethyl ether and dried in the oven at 80° C. to give the required product (30 g). $^1$H NMR (250 MHz, DMSO) δ 4.66 (2H, broad peak), 8.66 (1H, m), 8.84 (1H, d, J=2.5 Hz), 9.13 (1H, d, J=2.5 Hz), 10.15 (1H, broad peak); MS (ES$^+$) m/e 139 [MH$^+$].

e) 6-Chloro-7-phenyl-3-(pyrazin-2-yl)-1,2,4-triazolo[4,3-b]pyridazine

The product from Example 1 step b) (1 g, 4.46 mmol) was suspended in xylene (25 ml) with pyrazine-2-hydrazide (074 g, 5.35 mmol) and triethylamine hydrochloride (0.61 g, 4.46 mmol) and the reaction mixture was heated at reflux for 2 days. The solvent was removed under high vacuum, and the residue was dissolved in dichloromethane, basified with sodium bicarbonate and the aqueous extracted with dichloromethane (2×150 ml). The combined organic layers were washed with brine, dried (MgSO$_4$), filtered and evaporated. The residue was purified by silica gel chromatography using 0–40% ethyl acetate in dichloromethane as eluent to give the required product (0.249 g). $^1$H NMR (250 MHz, DMSO) δ 7.56 (5H, m), 8.43 (1H, s), 8.87 (1H, d, J=2.5 Hz), 8.96 (1H, d, J=2.5 Hz), 9.49 (1H, d J=2.5 Hz); MS (ES$^+$) m/e 309 [MH$^+$].

f) 6-(1-Methyl-1H-1,2,4-triazol-3-ylmethoxy)-7-phenyl-3-(pyrazin-2-yl)-1,2,4-triazolo[4,3-b]pyridazine To a solution of (1-methyl-1H-1,2,4-triazol-3-yl)methanol (prepared using the conditions described in EP-A-421210; 0.044 g, 0.39 mmol) in dimethyl formamide (10 ml) was added sodium hydride (0.016 g of a 60% dispersion in oil, 0.390 mmol) and the reaction mixture was stirred at room temperature under nitrogen for 0.5 h. After this time, the product from Example 1 step e) (0.1 g, 0.325 mmol) was added and the reaction mixture stirred for 2.5 h. The solvent was removed under high vacuum. Water (5 ml) was added to the residue and the solid produced was collected by filtration. The solid was recrystallised from ethyl acetate/ethanol to give the required product (0.049 g, m.p. 256.9–257.8° C.). $^1$H NMR (360 MHz, CDCl$_3$) δ 3.94 (3H, s), 5.62 (2H, s), 7.47 (3H, m), 7.67 (2H, m), 8.04 (1H, s), 8.10 (1H, s), 870 (1H, s), 8.84 (1H, s), 9.80 (1H, s) MS (ES$^+$) m/e 386 [MH$^+$].

EXAMPLE 2

6-(2-Methyl-2H-1,2,4-triazol-3-ylmethoxy)-7-phenyl-3-(pyrazin-2-yl)-1,2,4-triazolo[4,3-b]pyridazine This compound was prepared using procedures described in Example 1f), with (2-methyl-2H-1,2,4-triazol-3-yl)

methanol (prepared using the conditions described in EP-A-421210) being used instead of (1-methyl-1H-1,2,4-triazol-3-yl)methanol in step f.) m.p. 264° C. 1H NMR (360 MHz, CDCl$_3$) δ 3.83 (3H, s), 572 (2H, s), 7.50 (3H, m), 7.58 (2H, m), 7.88 (1H, s), 8.13 (1H, s), 875 (1H, s), 8.83 (1H, s), 9.69 (1H, s); MS (ES$^+$) m/e 386 [MH$^+$]. Anal. Found C, 59.21; H, 3.92; N, 3271. C$_{19}$H$_{15}$N$_9$O requires C, 59.36; H, 370; N, 32.69%.

EXAMPLE 3

7-Phenyl-3-(pyrazin-2-yl)-6-($^1$H-1,2,4-triazol-3-ylmethoxy)-1,2,4-triazolo[4,3-b]pyridazine a) [2-(2-(Trimethylsilyl)ethoxymethyl)-2H-1,2,4-triazol-3-yl]methanol 1-(2-Trimethylsilyl)ethoxy)methyl-1H-1,2,4-triazole (6.57 g) (prepared as described by Fugina et al., *Heterocycles*, 1992, 303–314) was dissolved in THF (110 ml) and cooled to −70° C. whereupon butyl lithium (23.12 ml of a 1.6 M solution in hexane) was added dropwise over 15 minutes keeping the temperature at −70° C. After 1 hour DMF (2.4 ml, 1 mol eq) was added and the reaction mixture was allowed to warm to 0° C. over 30 minutes. Saturated ammonium chloride solution (300 ml) was added and the mixture was extracted with ethyl acetate (2×300 ml). The organic layer was dried (Na$_2$SO$_4$), filtered and concentrated in vacuo to give a clear oil (6.5 g). This oil was dissolved in methanol (120 ml) and sodium borohydride (1.08 ml, 1 mol eq) was added in portions over 20 minutes. After lh the solvent was removed under vacuum and the residue was partitioned between water (50 ml) and dichloromethane (2×100 ml). The combined organic layers were washed with brine (1×30 ml) and dried (Na$_2$SO$_4$), filtered and concentrated in vacuo to give a clear oil which was purified by chromatography on silica gel using 0–4% methanol in dichloromethane as eluent to give the required compound (5 g) as a clear oil. $^1$H NMR (250 MHz, CDC$_3$) δ 0.00 (9H, s), 0.93 (2H, t, J=8.2 Hz), 3.63 (2H, t, J=8.2 Hz), 4.87 (2H, s), 4.11 ($^1$H, br s), 5.28 (2H, s), 7.85 (1H, s).

b) 7-Phenyl-3-(pyrazin-2-yl)-6-[2-(2-(trimethylsilyl)ethoxymethyl)-2H-1,2,4-triazol-3-ylmethoxy]-1,2,4-triazolo[4,3-b]pyridazine This compound was prepared using the procedure described in Example 1f) with [2-(2-(trimethylsilyl)ethoxymethyl)-2H-1,2,4-triazol-3-yl]methanol being used instead of (1-methyl-1H-1,2,4-triazol-3-yl)methanol. $^1$H NMR (250 MHz, CDCl$_3$) δ 0.00 (9H, s), 0.84 (2H, t, J=8.2 Hz), 3.57 (2H, t, J=8.2 Hz), 5.55 (2H, s), 5.83 (2H, s), 7.55–7.68 (5H, m), 7.99 (1H, s), 8.20 (1H, s), 8.80 (1H, s), 8.90 (1H, s), 876 (1H, s).

c) 7-Phenyl-3-(pyrazin-2-yl)-6-(1H-1,2,4-triazol-3-ylmethoxy)-1,2,4-triazolo[4,3-b]pyridazine The product from Example 3 step b) (0.3 g) was suspended in ethanol (10 ml) with 2 N hydrochloric acid (21 ml) and heated at 65° C. for 5.5 h. Saturated sodium carbonate solution was added dropwise until a solid precipitated and this was collected by filtration and washed several times with water in the sinter funnel. The solid was recrystallised from methanol to give the required product (0.115 g, m.p. 255° C.). $^1$H NMR (360 MHz, DMSO) δ 5.64 (2H, s), 7.50 (3H, m), 7.62 (2H, m), 8.08 (1H, s), 8.16 (1H, s), 8.84 (1H, s), 8.90 (1H, s), 9.85 (1H, s); MS (ES$^+$) m/e 372 [MH$^+$]. Anal. Found C, 58.21; H, 3.53; N, 33.95. C$_{18}$H$_{13}$N$_9$O requires C, 58.16; H, 3.26; N, 33.39%.

EXAMPLE 4

3-(4-Methylthiazol-2-yl)-7-phenyl-6-(pyridin-2-ylmethoxy)-1,2,4-triazolo[4,3-b]pyridazine a) Methyl 4-methyl-2-thiazole carboxylate To a solution of 4-methylthiazole (10 g) in anhydrous tetrahydrofuran (200 ml) was added n-butyl lithium in hexane (34.65 ml of 1.6M solution) dropwise at −78° C. The solution was stirred at −78° C. for 1 hour, at which point carbon dioxide gas was passed through the solution for 20 mins at −78° C. The solution was then allowed to warm to room temperature over 2 hours, the precipitate was filtered off, dissolved in methanol (200 ml) and added to methanolic hydrogen chloride (200 ml). The solution was stirred at room temperature overnight. The solvent was removed under vacuum and diethyl ether was added to the residue. The resultant solid was filtered off to yield the title compound as a white solid (2.2 g). $^1$H NMR (250 MHz, DMSO) δ 2.44 (3H, s), 3.89 (3H, s), 7.74 (1H, s).

b) 4-Methyl-2-thiazole hydrazide

To a solution of methyl 4-methyl-2-thiazole carboxylate (step a, 2.1 g) in methanol (20 ml) was added hydrazine hydrate (3.2 ml) dropwise over 30 mins. The reaction mixture was stirred for 1.5 hours and the precipitate filtered off to yield the title compound as a white solid (1.6 g). $^1$H NMR (250 MHz, DMSO) δ 2.64 (3H, s), 4.82 (2H, bs), 7.79 (1H, s), 10.25 (1H, bs).

c) 3-(4-Methylthiazol-2-yl)-7-phenyl-6-(pyridin-2-ylmethoxy)-1,2,4-triazolo[4,3-b]pyridazine This compound was prepared using procedures described in Example 1 e), f), with 4-methyl-2-thiazole hydrazide being used instead of 2-pyrazine hydrazide in step e) and 2-pyridylcarbinol being used instead of (1-methyl-1H-1,2,4-triazol-3-yl)methanol in step f). $^1$H NMR (360 MHz, CDCl$_3$) δ 2.56 (3H, s), 5.69 (2H, s), 7.30 (1H, m), 7.50–7.59 (5H, m), 777 (3H, m), 8.39 (1H, s), 8.58 (1H, m); structure proven by NOE experiments; MS (ES$^+$) m/e 401 [MH$^+$]. Anal. Found C, 62.85; H, 3.84; N, 20.50. C$_{21}$H$_{16}$N$_6$OS +0.1% H$_2$O requires C, 62.70; H, 4.06; N, 20.89%.

EXAMPLE 5

7-t-Butyl-3-(5-methylisoxazol-3-yl)-6-(2-pyridylmethyloxy)-1,2,4-triazolo[4,3-b]pyridazine a) 4-t-Butyl-3-chloro-6-hydrazino pyridazine 4-t-Butyl-3,6-dichloropyridazine (Samaritoni, J. G.; *Org. Prep. & Proc. Intl.*, 1988, 20(2), 117–121) (16 g, 78 mmol) and hydrazine monohydrate (24.7 mL, 780 mmol) in ethanol (250 mL) were heated at reflux for 16 hours. The solvent was removed and hydrochloric acid (5M) was added and the resulting mixture was washed with dichloromethane. The aqueous layer was poured onto ice and ammonium hydroxide was added until the mixture was basic. The mixture was extracted with dichloromethane, dried (MgSO$_4$) filtered and evaporated to give a yellow solid (9.5 g, 61%) $^1$HNMR (360 MHz, CDCl$_3$) δ 1.46 (9H, s, t Bu), 378 (2H, br s, NH$_2$), 6.84 (1H, br s, NH), 7.10 (1H, s, ArH); MS (ES$^+$) m/e 201 [MH$^+$].

b) 7-t-Butyl-3-(5-methylisoxazol-3-yl)-6-chloro-1,2,4-triazolo[4,3-b]pyridazine

5-Methylisoxazole-3-carboxylic acid (318 mg, 2.5 mmol), bis-(2-oxo-3-oxazolidinyl) phosphinic chloride (637 mg, 2.5 mmol) and triethylamine (505 mg, 5.0 mmol) were added successively to a mixture of the preceding hydrazinopyridazine (500 mg, 2.5 mmol) and dichloromethane (20 ml). The reaction was stirred for 16 hours and then partitioned between butanol and sodium carbonate solution. The butanol extract was washed with water and evaporated to leave a residue which was suspended in xylene. Triethylamine hydrochloride (386 mg) was added and the reaction was refluxed for 16 hours. The xylene -was removed by evaporation and the residue was dissolved in dichloromethane and washed with water, dried (MgSO$_4$), filtered and evaporated. The residue was purified by column chromatography on silica gel by gradient elution with methanol/dichloromethane (0.5%→1.5% methanol/dichloromethane)

to yield the title-product (265 mg), $^1$HNMR (250 MHz, CDCl$_3$) δ 1.56 (9H, s, t-Bu), 2.59 (3H, s, Me), 6.86 (1H, s, ArH); MS [ES$^+$] m/e 292 [MH]$^+$.

c) 7-t-Butyl-3-(5-methylisoxazol-3-yl)-6-(2-pyridylmethyloxy)-1,2,4-triazolo[4,3-b]pyridazine Pyridine-2-methanol (224 mg, 2 mmol) in N,N-dimethylformamide (15 ml) was stirred with sodium hydride (60% dispersion in oil, 80 mg, 2 mmol) for 2 hours. The preceding iminochloride (265 mg, 0.91 mmol) was added and the mixture was stirred for 2 hours after which the solvent was removed by evaporation. The residue was dissolved in dichloromethane and was washed with water, dried (MgSO$_4$), filtered and evaporated. The residue was purified by column chromatography on silica gel by gradient elution (0.5–2% methanoldichloromethane) to yield the title-compound (150 mg, 50%), 1HNMR (360 MHz, CDCl$_3$) δ 1.47 (9H, s, t-Bu), 2.46 (3H, s, Me), 5.68 (2H, s, CH$_2$), 6.79 (1H, s, ArH), 7.28 (1H, m, ArH), 7.67 (1H, d, J=7.7 Hz, ArH), 7.76 (1H, m, ArH), 7.98 (1H, s, ArH), 8.66 (1H, m, ArH); MS [ES$^+$] m/e 365 [MH]$^+$; Anal. Found: C, 62.41; H, 5.42; N, 22.52. C$_{19}$H$_{20}$N$_6$O$_2$ requires C, 62.23; H, 5.57; N, 22.91%.

EXAMPLE 6

7-t-Butyl-3-(5-methylisoxazol-3-yl)-6-(1-methyl-1,2,4-triazol-3-yl) methyloxy-1,2,4-triazolo[4,3-b]pyridazine a) 7-t-Butyl-6-chloro-3-dichloromethyl-1,2,4-triazolo[4,3-b]pyridazine 4-t-Butyl-3-chloro-6-hydrazinopyridazine (9.5 g, 48 mmol) and dichloroacetic acid (20 ml) were heated in toluene (130 ml) under Dean Stark conditions for 2.5 hours. The toluene was removed and the residue was poured into water to precipitate the product as a brown solid. The product was purified by chromotography on silica gel using 10% ethyl acetate/dichloromethane as eluant to yield a yellow solid (10.4 g, 74%), $^1$H NMR (250 MHz, CDCl$_3$) δ 1.59 (9H, s, t-Bu), 6.01 (1H, s, CM), 8.37 (1H, s, ArH); MS (ES$^+$) m/e 293 [MH]$^+$.

b) 7-t-Butyl-3-carboxamidoxime-6-chloro-1,2,4-triazolo[4,3-b]pyridazine

The preceding product (10.4 g, 36 mmol) was treated with hydroxylamine hydrochloride (24.8 g, 360 mmol) in a mixture of trifluoroacetic acid (110 ml) and water (100 ml) at reflux for 24 hours. The trifluoroacetic acid was evaporated and the solid residue was filtered off, washed with water and recrystallised from ethanol to yield a white solid (4.7 g, 52%), $^1$HNMR (250 MHz, d$_6$-DMSO) δ 1.50 (9H, s, t-Bu), 8.35 (1H, s, CH), 8.49 (1H, s, CH), 12.40 (1H, s, OH); MS (ES$^+$) m/e 254 [MH]$^+$.

c) 7-t-Butyl-3-carboxamidochloroxime-6-chloro-1,2,4-triazolo[4,3-b]pyridazine

The preceding aldoxime (47 g, 18.6 mmol) was suspended in N,N-dimethylformamide. 10 ml of air saturated with hydrogen chloride was bubbled through the reaction mixture and N-chlorosuccinimide (2.72 g, 20.4 mmol) was added. The reaction was heated to 50° C. and then allowed to cool and stir for two hours. The reaction mixture was poured into water to precipitate the product as a white solid (3.9 g, 72%), $^1$H NMR (250 MHz, d$_6$-DMSO) δ 1.50 (9H, s, t-Bu), 8.41 (1H, s, ArH), 13.44 (1H, s, OH); MS (ES$^+$) m/e 288 [MH]$^+$.

d) 7-t-Butyl-3-(5-methylisoxazol-3-yl)-6-chloro-1,2,4-triazolo[4,3-b]pyridazine

Propyne (~2 ml) was condensed into dichloromethane (100 ml) and the preceding chloroxime (1.0 g, 3.5 mmol) was added followed by a solution of triethylamine (0.5 ml) in dichloromethane (100 ml) over 0.5 hours. The reaction mixture was washed with water, dried and evaporated to yield a solid which was purified by chromatography on silica gel eluting with ethyl acetate/dichloromethane (3:7) to yield a cream solid (0.88 g, 86%). $^1$H NMR (250 MHz, CDCl$_3$) δ 1.57 (9H, s, t-Bu), 2.58 (3H, s, Me), 6.86 (1H, s, ArH), 8.20 (1H, s, ArH). MS (Es$^+$) m/e 292 [MH]$^+$.

e) 7-t-Butyl-3-(5-methylisoxazol-3-yl)-6-(1-methyl-1,2,4-triazol-3-yl) methoxy-1,2,4-triazolo[4,3-b]pyridazine Prepared in a similar manner as Example 5(c) using 3-hydroxymethyl-1-methyl-1,2,4-triazole. m.p. 221–223° C.; $^1$H NMR (250 MHz, CDCl$_3$) δ 1.43 (9H, s, t-Bu), 2.58 (3H, s, Me), 3.96 (3H, s, Me), 5.62 (2H, s, CH$_2$), 6.94 (1H, s, ArH), 7.97 (1H, s, ArH), 8.07 (1H, s, ArH); MS (ES$^+$) m/e 369 [MH]$^+$; Anal. Found: C, 55.21; H, 5.18; N, 30.04. C$_{17}$H$_{20}$N$_8$O$_2$ requires C, 55.43; H, 5.47; N, 30.42%.

EXAMPLE 7

7-t-Butyl-3-(5-methylisoxazol-3-yl)-6-(1-methyl-1,2,3-triazol-$^4$-yl) methyloxy-1,2,4-triazolo[4,3-b] pyridazine a) 7-t-Butyl-3-(5-methylisoxazol-3-yl)-6-chloro-1,2,4-triazolo[4,3-b]pyridazine t-Butyldimethylsilyltrifluoromethane sulfonate (7.8 ml, 34 mmol), triethylamine (4.7 ml, 34 mmol) and acetone (2.5 ml, 34 mmol) were stirred together at 20° C. for 1 hour. The chloroxime from Example 6(c) (5 g, 17 mmol) was added and a solution of triethylamine (12 ml) in dichloromethane (120 ml) was added over 1 hour. The solvent was removed and the residue was dissolved in methanol (120 ml), concentrated hydrochloric acid (36 ml) and the mixture stirred for 2 hours. The methanol was removed and the residue was extracted into dichloromethane, washed with water, dried MgSO$_4$), filtered and evaporated. The residue was purified by chromatography on silica gel using ethyl acetate/ dichloromethane as elutant to yield a white solid (4.2 g, 85%). $^1$H NMR (250 MHz, CDCl$_3$) δ 1.57 (9H, s, t-Bu), 2.58 (3H, s, Me) 6.86 (1H, s, ArH), 8.20 (1H, s, Ark). MS (ES$^+$) m/e 292 [MH]$^+$.

b) 7-t-Butyl-3-(5-methylisoxazole-3-yl)-6-(1-methyl-1,2,3-triazol-4-yl) methyloxy-1,2,4-triazolo[4,3-b]pyridazine Prepared in a similar manner as Example 5(c) using 4-hydroxymethyl-1-methyl-1,2,3-triazole, mp 219–221° C.; $^1$HNMR (250 MHz, CDCl$_3$) δ 1.41 (9H, s, t-Bu), 2.60 (3H, s, Me), 4.09 (3H, s, Me), 5.69 (2H, s, CH$_2$), 6.87 (1H, s, ArH), 7.94 (1H, s, ArH), 8.62 (1H, s, ArH); MS (ES$^+$) m/e 369 [MH]$^+$.

The following two compounds were made by analogous methods using the appropriate starting materials.

7-t-Butyl-3-(isoxazol-3-yl)-6-(1-methyl-1,2,4-triazol-3-yl)methyloxy-1,2,4-triazolo[4,3-b] pyridazine $^1$H NMR (250 MHz, CDCl$_3$) δ 1.44 (s, 9H, tBu), 3.95 (s, 3H, Me), 5.63 (s, 2H, CH$_2$), 7.35 (d, 1H, ArH), 7.98 (s, 1H, ArH), 8.10 (s, 1H, ArH), 8.64 (d, 1H, ArH). mp 222–224° C.

7-(1-Methylcyclobut-1-yl)-3-(5-methylisoxazol-3-yl)-6-(1-methyl-1,2,3-triazol-4-yl)methyloxy-1,2,4-triazolo[4,3-b]pyridazine $^1$H NMR (500 MHz, DMSO) δ 1.45 (s, 3H, CH$_3$), 172–174 (m, 1H, CH), 1.98–2.02 (m, 2H, CH$_2$), 2.06–2.10 (m, 1H, CH), 2.35–2.40 (m, 2H, CH$_2$), 2.58 (s, 3H, CH$_3$), 4.07 (s, 3H, CH$_2$), 5.55 (s, 2H, CH$_2$), 7.15 (s, 1H, ArH) 7.90 (s, 1H, ArH), 8.28 (s, H, ArH). mp 246–248° C.

What is claimed is:

1. A compound represented by formula IIB, or a salt thereof:

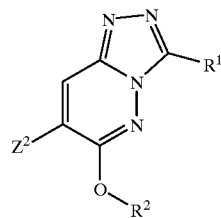

(IIB)

wherein:
R¹ represents a five-membered heteroaromatic ring selected from oxazole, thiazole, isoxazole, isothiazole, imidazole, pyrazole, oxadiazole, thiadiazole, triazole and tetrazole; or
R¹ represents a six-membered heteroaromatic ring selected from pyrazine, pyrimidine and pyridazine;
wherein said five-membered or six-membered heteroaromatic ring is optionally substituted by one or more $C_{1-6}$alkyl, phenyl($C_{1-6}$)alkyl, naphthyl($C_{1-6}$)alkyl, pyridyl($C_{1-6}$)alkyl, halogen, halo($C_{1-6}$)alkyl, cyano, cyano($C_{1-6}$)alkyl, hydroxy, hydroxymethyl, $C_{1-6}$alkoxy, $C_{3-7}$cycloalkyl($C_{1-6}$)alkoxy, $C_{3-7}$cycloalkoxy, amino($C_{1-6}$)alkyl, di($C_{1-6}$)alkylamino($C_{1-6}$)alkyl, di($C_{1-6}$)alkylaminocarbonyl($C_{1-6}$)alkyl, N-($C_{1-6}$)alkylpiperidinyl, pyrrolidinyl($C_{1-6}$)alkyl, piperazinyl($C_{1-6}$)alkyl, morpholinyl($C_{1-6}$)alkyl, di($C_{1-6}$)alkylmorpholinyl($C_{1-6}$)alkyl or imidazolyl($C_{1-6}$)alkyl substituents; and
R² represents pyridinyl($C_{1-6}$)alkyl, imidazolyl($C_{1-6}$)alkyl, or triazolyl($C_{1-6}$)alkyl, any of which groups may be optionally substituted by one or more $C_{1-6}$alkyl, phenyl($C_{1-6}$)alkyl, naphthyl($C_{1-6}$)alkyl, pyridyl($C_{1-6}$)alkyl, halogen, halo($C_{1-6}$)alkyl, cyano, cyano($C_{1-6}$)alkyl, hydroxy, hydroxymethyl, $C_{1-6}$alkoxy, $C_{3-7}$cycloalkyl($C_{1-6}$)alkoxy, $C_{3-7}$cycloalkoxy, amino($C_{1-6}$)alkyl, di($C_{1-6}$)alkylamino($C_{1-6}$)alkyl, di($C_{1-6}$)alkylaminocarbonyl($C_{1-6}$)alkyl, N-($C_{1-6}$)alkylpiperidinyl, pyrrolidinyl($C_{1-6}$)alkyl, piperazinyl($C_{1-6}$)alkyl, morpholinyl($C_{1-6}$)alkyl, di($C_{1-6}$)alkylmorpholinyl($C_{1-6}$)alkyl or imidazolyl($C_{1-6}$)alkyl substituents; and
Z² is pyridyl, tertiary butyl, cyclobutyl or methylcyclobutyl.

2. A compound according to claim 1 wherein:
R¹ is isoxazolyl or oxadiazolyl optionally substituted by chlorine or methyl; and
R² is pyridinyl($C_{1-6}$)alkyl; or imidazolyl($C_{1-6}$)alkyl or triazolyl($C_{1-6}$)alkyl optionally substituted by methyl or benzyl.

3. A compound selected from:
7-t-butyl-3-(5-methylisoxazol-3-yl)-6-(2-pyridylmethyloxy)-1,2,4-triazolo[4,3-b]pyridazine;
7-t-butyl-3-(5-methylisoxazol-3-yl)-6-(1-methyl-1,2,4-triazol-3-yl)methyloxy-1,2,4-triazolo[4,3-b]pyridazine;
7-t-butyl-3-(5-methylisoxazol-3-yl)-6-(1-methyl-1,2,3-triazol-4-yl)methyloxy-1,2,4-triazolo[4,3-b]pyridazine;
or a salt thereof.

4. A compound selected from:
6-(1-methyl-1H-1,2,4-triazol-3-ylmethoxy)-7-phenyl-3-(pyrazin-2-yl)-1,2,4-triazolo[4,3-b]pyridazine;
6-(2-methyl-2H-1,2,4-triazol-3-ylmethoxy)-7-phenyl-3-(pyrazin-2-yl)-1,2,4-triazolo[4,3-b]pyridazine;
7-phenyl-3-(pyrazin-2-yl)-6-(1H-1,2,4-triazol-3-ylmethoxy)-1,2,4-triazolo[4,3-b]pyridazine;
3-(4-methyltriazol-2-yl)-7-phenyl-6-(pyridin-2-ylmethoxy)-1,2,4-triazolo[4,3-b]pyridazine;
or a salt thereof.

5. A pharmaceutical composition for treating anxiety or for enhancing cognition which comprises a therapeutically effective amount of a compound of claim 1, or a salt thereof, and a pharmaceutically acceptable excipient.

6. A method of treating anxiety in a subject suffering from anxiety which comprises administering to that subject a therapeutically effective amount of a compound of claim 1, or a salt thereof.

7. A method of enhancing spatial learning in a subject suffering from a cognition deficit which comprises administering to that subject a theraeutically effective amount of a comnpound of claim 1, or a salt thereof.

8. A method of treating cognition in a subject suffering from Alzheimer's Disease which comprises administering to that subject a therapeutically effective amnount of a compound of claim 1 or a salt thereof.

* * * * *